US00PP36473P2

(12) United States Plant Patent
Hartman

(10) Patent No.: US PP36,473 P2
(45) Date of Patent: Feb. 18, 2025

(54) ***CALADIUM* PLANT NAMED 'SCH OF16-414'**

(50) Latin Name: ***Caladium* X *hortulanum***
Varietal Denomination: SCH OF16-414

(71) Applicant: Robert Dale Hartman, Lake Placid, FL (US)

(72) Inventor: Robert Dale Hartman, Lake Placid, FL (US)

( * ) Notice: Subject to any disclaimer, the term of this patent is extended or adjusted under 35 U.S.C. 154(b) by 0 days.

(21) Appl. No.: 18/657,777

(22) Filed: May 7, 2024

(51) Int. Cl.
*A01H 5/12* (2018.01)
*A01H 6/10* (2018.01)

(52) U.S. Cl.
USPC ..... Plt./373

(58) Field of Classification Search
USPC ..... Plt./373
See application file for complete search history.

(56) References Cited

U.S. PATENT DOCUMENTS

PP31,568 P2 * 3/2020 Hartman ..... A01H 6/10
Plt./373

* cited by examiner

*Primary Examiner* — Karen M Redden
(74) *Attorney, Agent, or Firm* — C. Anne Whealy

(57) ABSTRACT

A new and distinct cultivar of *Caladium* plant named 'SCH OF16-414', characterized by its upright plant habit and intermediate to tall in height; dense, leafy and bushy appearance; vigorous growth habit and rapid growth rate; fancy-type leaves that are greyed yellowish green in color with red-colored venation and dark green-colored margins; and petioles that are tannish pink in color with dense greenish brown-colored streaks, stippling and tessellations.

4 Drawing Sheets

Figure 1:
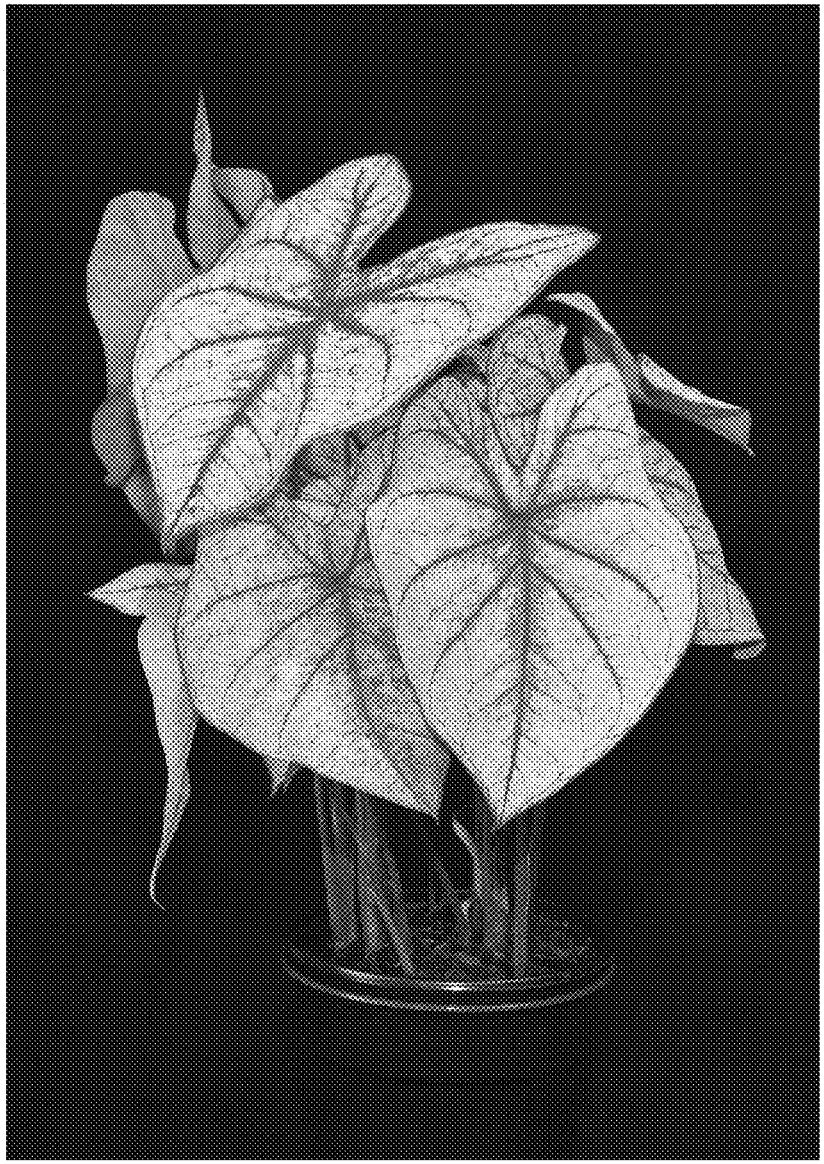

Botanical designation: *Caladium* X *hortulanum*.
Cultivar denomination: 'SCH OF16-414'.

BACKGROUND OF THE INVENTION

The present invention relates to a new and distinct cultivar of *Caladium* plant, botanically known as *Caladium* X *hortulanum*, commercially referred to as a fancy leaf-type *Caladium* and hereinafter referred to by the name 'SCH OF16-414'.

The objective of the Inventor's breeding program is to create new *Caladium* plants that have uniform plant habit, exceptional container and garden performance and attractive and unique leaf coloration.

The new *Caladium* plant originated from a cross-pollination made by the Inventor in April 2015 in Avon Park, Florida of *Caladium* X *hortulanum* 'Frieda Hemple', not patented, as the female, or seed, parent with *Caladium* X *hortulanum* 'Southern Charm', disclosed in U.S. Plant Pat. No. 27,942, as the male, or pollen, parent. The new *Caladium* plant was discovered and selected by the Inventor as a single plant within the progeny of the stated cross-pollination in a controlled outdoor nursery environment in Avon Park, Florida in September, 2016.

Asexual reproduction of the new *Caladium* plant by "chipping" the tubers (cutting the tuber into segments with each segment containing an axillary bud and tuber cortical tissue) in a controlled outdoor nursery environment in Zolfo Springs, Florida since April, 2017 has shown that the unique features of this new *Caladium* plant are stable and reproduced true to type in successive generations of asexual reproduction.

SUMMARY OF THE INVENTION

Plants of the new *Caladium* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'SCH OF16-414'. These characteristics in combination distinguish 'SCH OF16-414' as a new and distinct *Caladium* plant:

1. Upright plant habit and intermediate to tall in height; dense, leafy and bushy appearance.
2. Vigorous growth habit and rapid growth rate.
3. Fancy-type leaves that are greyed yellowish green in color with red-colored venation and dark green-colored margins.
4. Petioles that are tannish pink in color with dense greenish brown-colored streaks, stippling and tessellations.

Plants of the new *Caladium* differ primarily from plants of the female parent, 'Frieda Hemple', in the following characteristics:

1. Plants of the new *Caladium* are taller than plants of 'Frieda Hemple'.
2. Leaves of plants of the new *Caladium* are larger than leaves of plants of 'Frieda Hemple'.
3. Leaves of plants of the new *Caladium* are greyed yellowish green in color with red-colored venation and dark green-colored margins whereas leaves of plants of 'Frieda Hemple' are medium green in color with bright red-colored centers and venation.
4. Petioles of plants of the new *Caladium* are tannish pink in color with dense greenish brown-colored streaks, stippling and tessellations whereas petioles of plants of 'Frieda Hemple' are tannish pink in color with dense brownish black-colored stippling and streaks.

Plants of the new *Caladium* differ primarily from plants of the male parent, 'Southern Charm', in the following characteristics:

1. Plants of the new *Caladium* are taller than plants of 'Southern Charm'.
2. Leaves of plants of the new *Caladium* are greyed yellowish green in color with red-colored venation and dark green-colored margins whereas leaves of plants of 'Southern Charm' are grey green in color with dark green-colored margins and red purple-colored venation and areas surrounding the venation.
3. Petioles of plants of the new *Caladium* are tannish pink in color with dense greenish brown-colored streaks, stippling and tessellations whereas petioles of plants of 'Southern Charm' are green and tinged with pink in color.

Plants of the new *Caladium* can be compared to plants of *Caladium* X *hortulanum* 'White Queen', not patented. In side-by-side comparisons, plants of the new *Caladium* differ primarily from plants of 'White Queen' in the following characteristics:

1. Plants of the new *Caladium* are taller than plants of 'White Queen'.
2. Leaves of plants of the new *Caladium* are greyed yellowish green in color with red-colored venation and dark green-colored margins whereas leaves of plants of 'White Queen' are white in color with rose pink-colored venation and central areas surrounding the venation.
3. Petioles of plants of the new *Caladium* are tannish pink in color with dense greenish brown-colored streaks, stippling and tessellations whereas petioles of plants of 'White Queen' are almost black in color with tannish pink-colored stripes.

Plants of the new *Caladium* can also be compared to plants of *Caladium* X *hortulanum* 'Summer Breeze', disclosed in U.S. Plant Pat. No. 25,420. In side-by-side comparisons, plants of the new *Caladium* differ primarily from plants of 'Summer Breeze' in the following characteristics:

1. Plants of the new *Caladium* are taller than plants of 'Summer Breeze'.
2. Leaves of plants of the new *Caladium* are greyed yellowish green in color with red-colored venation and dark green-colored margins whereas leaves of plants of 'Summer Breeze' are white to creamy white in color with a central pink-colored blush, pink-colored venation and green-colored margins.
3. Petioles of plants of the new *Caladium* are tannish pink in color with dense greenish brown-colored streaks, stippling and tessellations whereas petioles of plants of 'Summer Breeze' are pink to tannish pink in color with faint greenish brown-colored streaks, stippling and tessellations.

BRIEF DESCRIPTION OF THE PHOTOGRAPHS

The accompanying photographs illustrate the overall appearance of the new *Caladium* plant showing the colors as true as it is reasonably possible to obtain in colored reproductions of this type. Colors in the photographs may differ slightly from the color values cited in the detailed botanical description which accurately describe the colors of the new *Caladium* plant.

The photograph on the first sheet (FIG. 1) is a side perspective view of a typical plant of 'SCH OF16-414' grown in a container that has had its tuber de-eyed prior to planting.

Figure 2:
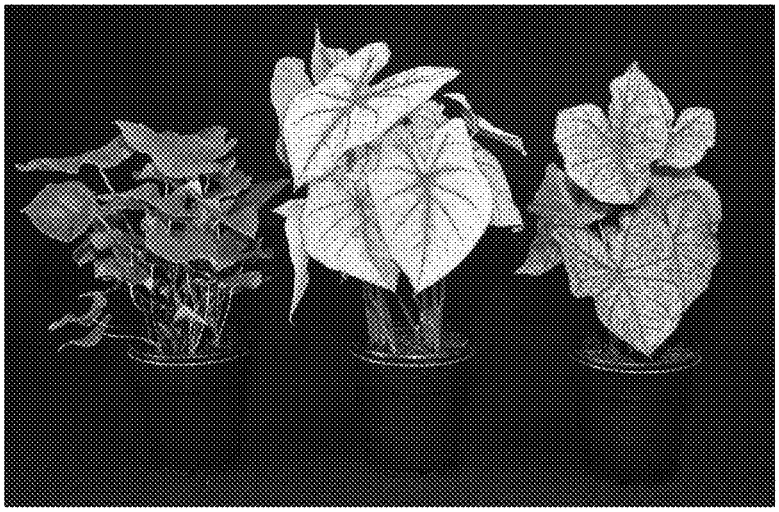

The photograph at the top of the second sheet (FIG. 2) is side perspective view of typical plants of the female parent, 'Frieda Hemple' (left), 'SCH OF16-414' (center) and the male parent, 'Southern Charm' (right).

Figure 3:
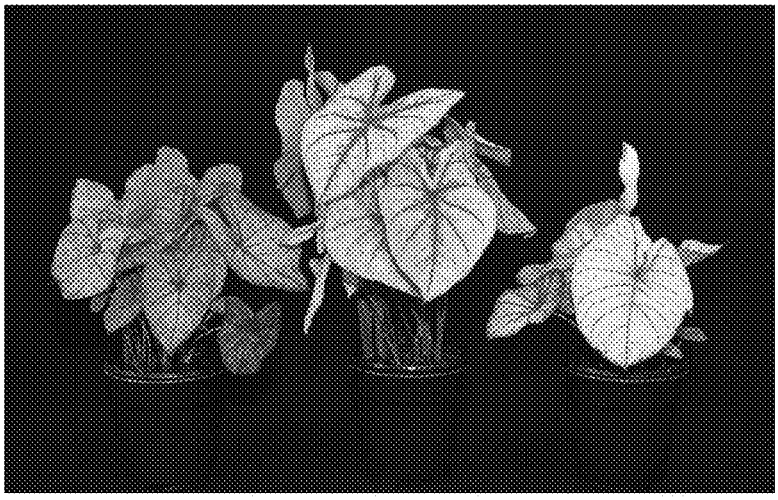

The photograph at the bottom of the second sheet (FIG. 3) is side perspective view of typical plants of 'White Queen' (left), 'SCH OF16-414' (center) and 'Summer Breeze' (right).

Figure 4:
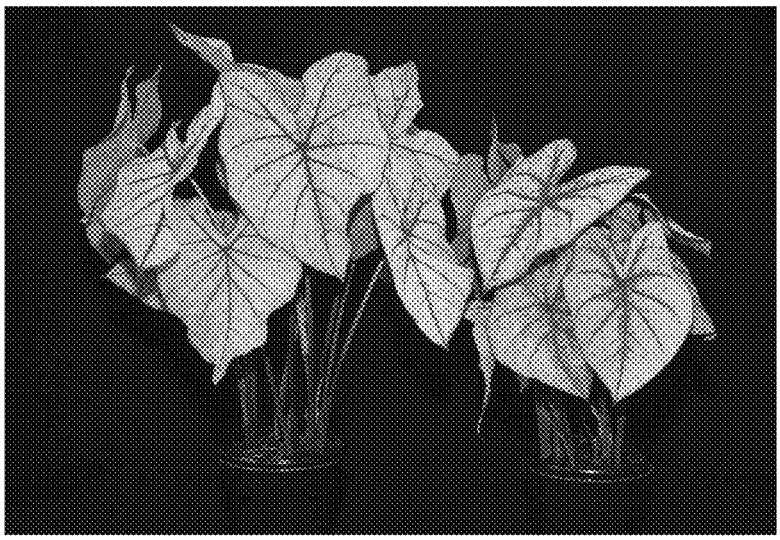

The photograph at the top of the third sheet (FIG. 4) is a comparison view of typical plants of 'SCH OF16-414' grown in containers, the plant on the left has not had its tuber de-eyed and the plant on the right has had its tuber de-eyed prior to planting.

Figure 5:
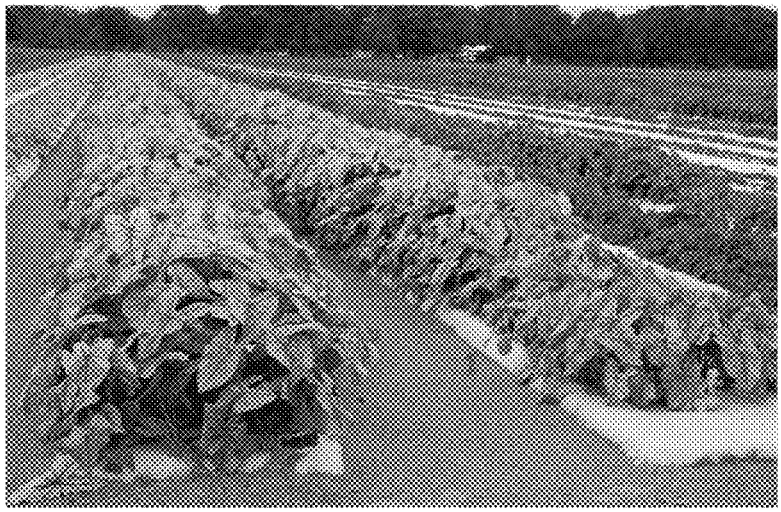

The photograph at the bottom of the third sheet (FIG. 5) is a side perspective view of typical plants of 'SCH OF16-414' grown in an open production field.

Figure 6:
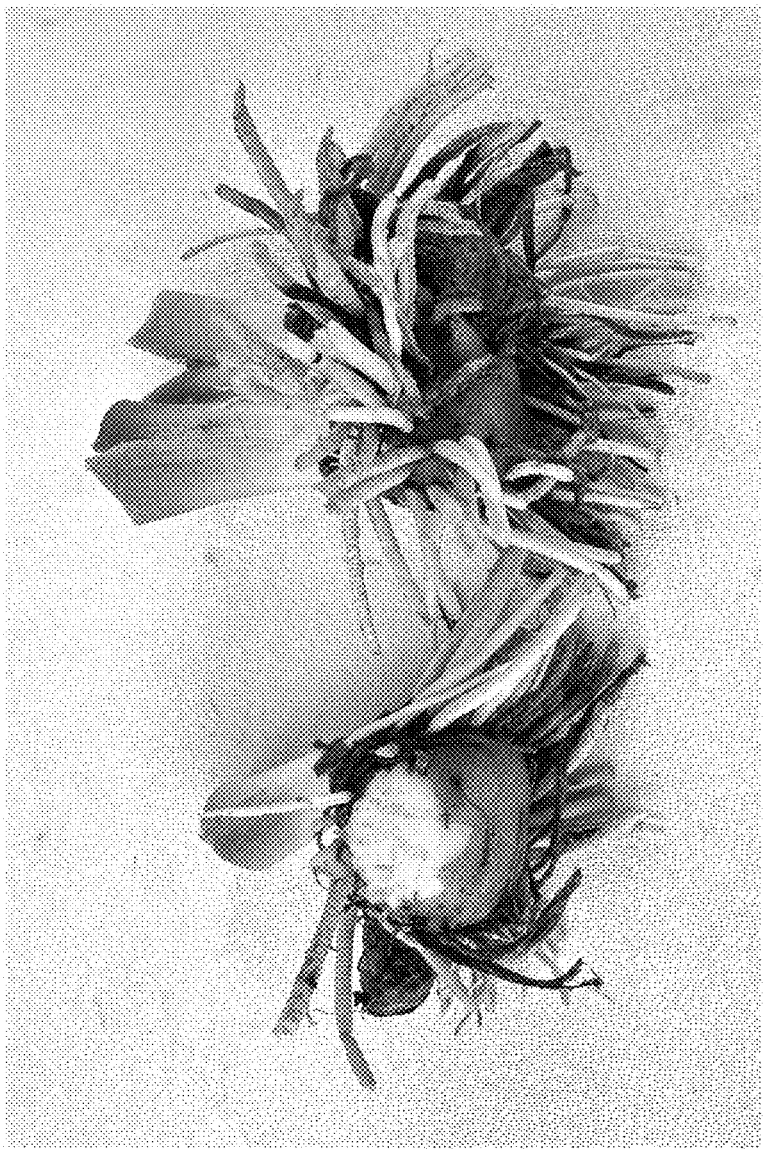

The photograph on the fourth sheet (FIG. 6) is a close-up view of typical freshly-harvested tubers with roots of 'SCH OF16-414'.

DETAILED BOTANICAL DESCRIPTION

The aforementioned photographs and following observations and measurements describe plants grown in 15-cm containers in a polypropylene-covered shade house (30% light reduction) in Avon Park, Florida and plants grown in ground beds under full sunlight conditions in an outdoor nursery in Crewsville, Florida. The plants were grown under cultural practices typical of commercial shade house and outdoor nursery production. During the production of the shade house-grown plants, day temperatures ranged from about 28° C. to 33° C., night temperatures ranged from about 22° C. to 25° C. and light levels were about 1,300 μmol. During the production of the outdoor nursery-grown plants, day temperatures ranged from about 29° C. to 35° C., night temperatures ranged from about 23° C. to 26° C. and full sunlight conditions. Plants grown in the shade house were five to six weeks old and plants grown in the outdoor nursery were seven months old when the photographs and the detailed description were taken. In the following description, color references are made to The Royal Horticultural Society Colour Chart, 2001 and 2015 Editions, except where general terms of ordinary dictionary significance are used.

Botanical classification: *Caladium* X *hortulanum* 'SCH OF16-414'.

Parentage:

*Female, or seed, parent.*—*Caladium* X *hortulanum* 'Frieda Hemple', not patented.

*Male, or pollen, parent.*—*Caladium* X *hortulanum* 'Southern Charm', disclosed in U.S. Plant Pat. No. 27,942.

Propagation:

*Type.*—By "chipping" the tubers.

*Time to initiate roots, summer.*—About seven to ten days at temperatures about 32° C.

*Time to initiate roots, winter.*—About two to three weeks at temperatures about 24° C.

*Tuber description* (*outdoor nursery-grown plants*).—Appearance: Multi-segmented and branched; individual segments are elliptic or irregular in shape. Height: About 4.3 cm to 4.9 cm. Diameter: About 5 cm to 5.2 cm. Segment height: About 2.5 cm. Segment diameter: About 1.6 cm. Axillary bud shape: Roughly triangular. Axillary bud height: About 4 mm to 6 mm. Axillary bud width: About 4 mm. Texture: Thick, starchy; somewhat brittle. Color: Periderm, freshly-harvested: Close to 199D and 200D. Periderm, dried: Close to 200A. Epidermis: Close to N170D flushed with close to 180D. Cortical tissue: Close to 10C to 10D. Axillary buds: Close to 38C to 38D. Root description: Relatively thick, fleshy contractile roots with few lateral branches; color, close to NN155D tinged with close to 185D; actual color of the roots is dependent on substrate composition, water quality, fertilizer type and formulation, substrate temperature and physiological age of roots; root density, moderately dense.

Plant description:

*Plant type*.—Herbaceous perennial; suitable as a potted plant in containers 15-cm to 25-cm and suitable as a landscape plant in shaded or full sunlight areas.

*Plant and growth habit*.—Upright plant habit; intermediate to tall in height; dense, leafy and bushy appearance; vigorous growth habit and rapid growth rate; potted plants finish in saleable form in about five to six weeks after planting tubers; leaf petioles and leaves arise from one or more growing points on tubers; leaf petioles initially upright and leaning outwardly with development.

*Plant height, from soil level to top of foliar plane, shade house-grown potted plants, tubers de-eyed*.—About 40 cm to 44 cm.

*Plant height, from soil level to top of foliar plane, shade house-grown potted plants, tubers not de-eyed*.—About 56 cm to 61 cm.

*Plant diameter, shade house-grown potted plants, tubers de-eyed*.—About 42 cm to 46 cm.

*Plant diameter, shade house-grown potted plants, tubers not de-eyed*.—About 40 cm to 47 cm.

*Number of shoots per plant, shade house-grown potted plants, tubers de-eyed*.—About four to seven develop per #1 tuber.

*Number of shoots per plant, shade house-grown potted plants, tubers not de-eyed*.—About three to four develop per #1 tuber.

*Cataphylls, shade house-grown potted plants*.—Length: About 5.5 cm to 8 cm. Width: About 9 mm. Shape: Wedge-shaped to lanceolate. Apex: Acute to acuminate. Base: Sheathing the stem. Texture, outer and inner surfaces: Smooth, glabrous. Color, outer and inner surfaces: Close to 200A to 200D.

Leaf description:

*Arrangement and type*.—Alternate; simple; fancy-type.

*Length, shade house-grown potted plants, tubers de-eyed*.—About 17.3 cm to 23.5 cm.

*Length, shade house-grown potted plants, tubers not de-eyed*.—About 18 cm to 26.5 cm.

*Width, shade house-grown potted plants, tubers de-eyed*.—About 10.9 cm to 16 cm.

*Width, shade house-grown potted plants, tubers not de-eyed*.—About 11.5 cm to 17.9 cm.

*Shape*.—Ovate with cordate tendencies.

*Apex*.—Acute to somewhat acuminate.

*Base*.—Sagittate-peltate, cordate.

*Margin*.—Entire; mostly flat with broad undulations.

*Texture and luster, upper surface*.—Smooth, glabrous; dull sheen.

*Texture and luster, lower surface*.—Smooth, glabrous; glaucous; dull sheen.

*Venation pattern*.—Pinnate and palmate.

*Color, shade house-grown potted plants*.—When developing and fully expanded leaves, upper surface: Ground color: Close to 191C, 194C, 194D, 195B and/or 195D; central mottling, close to 185A; if present, random flecks, close to 185A. Marginal areas: Close to 147A or 191C to 191D with random speckles, close to 155C, 191C, 191D or 194C; edges, close to 187B. Basal notch: Close to 187A. Midvein and lateral venation: Close to 53A tinged with close to 187B; areas surrounding veins, close to 48A and/or 53C to 53D; smaller veins, close to 147A, may be tinged with close to 53A and/or 187B. When developing and fully expanded leaves, lower surface: Ground color: Close to 147B, 147C, 147D, 150D, 155B, 191A, 191B and/or 145C; if present, random flecks, close to 150D; central mottling, close to 36C to 36D and 51B to 51C. Marginal areas: Close to 191A or 194B with random speckles, close to 150D; edges, close to 187A. Basal notch: Close to 187A. Midvein: Close to 182C and 183A; areas surrounding midvein, close to 51B to 51C and 182C. Lateral venation: Close to 191A and N189A; areas surrounding veins, close to 51B to 51C and 182C; smaller veins, close to 147A to 147B.

*Petioles*.—Aspect: Initially upright and straight and leaning outwardly with development; flexible. Length, shade house-grown potted plants, tubers de-eyed: About 30 cm to 37 cm. Length, shade house-grown potted plants, tubers not de-eyed: About 32.9 cm to 50 cm. Diameter, distally, shade house-grown potted plants, tubers de-eyed: About 3 mm to 4.5 mm. Diameter, proximally, shade house-grown potted plants, tubers de-eyed: About 5 mm to 7.5 mm. Diameter, distally, shade house-grown potted plants, tubers not de-eyed: About 4.5 mm to 5 mm. Diameter, proximally, shade house-grown potted plants, tubers not de-eyed: About 8.5 mm to 11 mm. Texture: Smooth, glabrous; distally, glaucous, and proximally, slightly glossy. Color, shade house-grown potted plants: Close to 182D, 199A and/or 147A tinged, streaked and tessellated with close to 147A tinged with close to 200A; just below the leaf junction, close to 182B and 177A tinged, streaked and mottled with close to 183A. Wing length, shade house-grown potted plants: About 7 cm to 11 cm. Wing diameter, shade house-grown potted plants: About 7.5 mm to 10 mm. Texture and luster, outer and inner surfaces: Smooth, glabrous; dull. Wing color, shade house-grown potted plants: Outer surface: Close to N155C to N155D densely streaked and stippled with close to 147A tinged with close to 200A. Inner surface: Close to 155A and 195D; colors and patterns from the outer surface are visible on the inner surface.

Inflorescence description: To date, inflorescence development has not been observed on plants of the new *Caladium*.

Pathogen tolerance/resistance: Plants of the new *Caladium* have been observed to have average tolerance to *Pythium* Root Rot and average tolerance to *Xanthomonas* Leaf Spot. Plants of the new *Caladium* have not been observed to have tolerance/resistance to other pathogens common to *Caladium* plants.

Temperature tolerance: Plants of the new *Caladium* have been observed to tolerate temperatures ranging from about 7° C. to about 40° C. and are suitable for USDA Hardiness Zones 8A to 11. In cooler zones, tubers can be "lifted" prior to first freeze and stored in a cool dry environment to overwinter for re-planting the following spring.

It is claimed:

1. A new and distinct *Caladium* plant named 'SCH OF16-414' as illustrated and described herein.

* * * * *